United States Patent [19]

Kluger

[11] Patent Number: 4,733,657

[45] Date of Patent: Mar. 29, 1988

[54] APPARATUS FOR ALIGNING A SPINAL COLUMN HAVING DAMAGED VERTEBRAE

[76] Inventor: Patrick Kluger, Fichtenstr.5, 3590 Bad Wildungen, Fed. Rep. of Germany

[21] Appl. No.: 723,856

[22] Filed: Apr. 16, 1985

[30] Foreign Application Priority Data

Apr. 16, 1984 [DE] Fed. Rep. of Germany ....... 3414374

[51] Int. Cl.⁴ .............................................. A61F 5/04
[52] U.S. Cl. .......................... 128/92 YM; 128/92 ZZ
[58] Field of Search ..................... 128/69, 84 R, 92 B; 269/328

[56] References Cited

U.S. PATENT DOCUMENTS

| | | | |
|---|---|---|---|
| Re. 31,809 | 1/1985 | Danieletto | 128/92 B |
| 2,238,870 | 4/1941 | Haynes | 128/84 R |
| 2,439,995 | 4/1948 | Thrailkill | 128/84 R |
| 3,941,365 | 3/1976 | Frymoyer | 269/328 |
| 4,433,677 | 2/1984 | Ulrich | 128/69 |
| 4,445,513 | 5/1984 | Ulrich | 128/69 |
| 4,541,422 | 9/1985 | Zbikowski | 128/92 B |

FOREIGN PATENT DOCUMENTS

| | | | |
|---|---|---|---|
| 2649042 | 9/1978 | Fed. Rep. of Germany | 128/69 |
| 780652 | 8/1957 | United Kingdom | 128/69 |
| 839515 | 6/1981 | U.S.S.R. | 128/92 B |
| 982681 | 12/1982 | U.S.S.R. | 128/92 B |
| 1063405 | 12/1983 | U.S.S.R. | 128/69 |

Primary Examiner—Clyde I. Coughenour
Attorney, Agent, or Firm—Roberts, Spiecens & Cohen

[57] ABSTRACT

Apparatus for straightening a spinal column having damaged vertebrae in which support bolts are inserted into the vertebrae on both sides of the damaged vertebrae comprising a guide shaft carrying first and second arms. One of the arms is displaceable on the guide shaft and the other arm is fixed on the guide shaft. A receiving sleeve is displaceable on each arm in mutually perpendicular planes and receives an extension rod which is detachably seated in a respective support bolt.

5 Claims, 3 Drawing Figures

4,733,657

APPARATUS FOR ALIGNING A SPINAL COLUMN HAVING DAMAGED VERTEBRAE

FIELD OF THE INVENTION

The present invention relates to an apparatus for the aligning of a spinal column having damaged vertebrae, by which support bolts are inserted into the vertebrae on both sides of the damaged vertebra in order to apply a support system.

BACKGROUND

As is known, a spinal column having damaged vertebrae must be helped back to stability by inserting a support system into the vertebrae on both sides of the damaged vertebra. In this case, the aligning of the spinal column must first be effected, followed by the stabilizing thereof. The stabilizing of the spinal column is effected in the manner that the damaged vertebra is mechanically bridged. For this purpose, turnbuckles are used which connect together support bolts which have been inserted, one above the other, into the sound vertebrae and thus assume the transmission of forces. The turnbuckles consist of a threaded sleeve into the ends of which screw bolts of opposite thread are screwed. In this way, the turnbuckle which connects the support bolts can be used for aligning and stabilizing by turning the threaded sleeve.

Since relatively long support bolts are required for the alignment of the spinal column, due to the lever forces required, the protruding lengths of the support bolts must be cut off after the stabilizing of the spinal column has been effected so that the entire support system can be implanted. This, however, results in vibrations in the system; furthermore, it is unavoidable that metal dust enters the wound. In addition, the support system represents a large amount of material which must be implanted. Furthermore, the operation is technically difficult because of the large number of screws to be inserted into the depth of the wound and increases the time required for the operation.

SUMMARY OF THE INVENTION

The object of the present invention therefore is to effect the aligning of the spinal column by means other than those which serve for the stabilizing.

In accordance with the invention, the apparatus comprises one arm which is displaceable on a guide shaft and a second arm which is fixed on the guide shaft, each arm bearing at its end a receiving sleeve which is displaceable in planes which are perpendicular to each other, each sleeve receiving an extension bar which is placed on the support bolt which has been arranged in the vertebra.

In detail, the construction is such that the receiving sleeve bears a resting surface which is detachably fastened with detents on a support surface, the support surface being arranged in such a manner that it can be pivoted on the arm and locked in position. In this way, the support surface can, first of all, be adjusted around the axis of the pivot and furthermore the resting surface with its detents can also be displaced on the support surface itself. The attachment of the resting surface to the support surface is effected in general by a threaded connection, for which a corresponding hole must then be provided in the resting surface.

The guide shaft on which the two arms are placed bears a thread which receives a setting nut which acts on the displaceable arm.

When the extension bars have been placed on the support bolts then the straightening of the spinal column can be effected in the manner that the receiving sleeves of the apparatus are pushed onto the extension rods and fastened there. By turning the setting nuts the two arms are moved towards or away from each other so that a corresponding bending moment is exerted on the support bolts, which leads to a straightening or aligning of the spinal column.

The support bolt bears coaxially a thread for the attachment of the extension bar. Furthermore, the support bolt bears a fastening surface for a turnbuckle.

When the spinal column has been aligned, the spinal column is then stabilized by applying a turnbuckle or a fixing bar to the fastening surface of the support bolt, which surface is provided with detents. Since the extension bars are removable, the support bolt can therefore be relatively short since it is not required for the straightening of the spinal column but merely for the stabilizing thereof. There can also be used a turnbuckle which does not consist of a threaded sleeve with two screw bolts inserted at its ends but merely a turnbuckle consisting of clamping sleeve and screw bolt each of which has at its end a fastening surface with detents adapted to be placed on the fastening surfaces of the support bolts.

It is thus clear that for the straightening of the spinal column there is used a special apparatus which can be removed after the straightening has been effected, and no sawing off of the supporting bolts is necessary since the extension bars are arranged removably on the relatively short support bolts.

The arms are angular and curved in space. In this way, the operating field is more easily accessible since the arms extend away from the wound.

BRIEF DESCRIPTION OF THE FIGURES OF THE DRAWING

One illustrative embodiment is shown in the drawing, in which.

DETAILED DESCRIPTION

Figure 1:
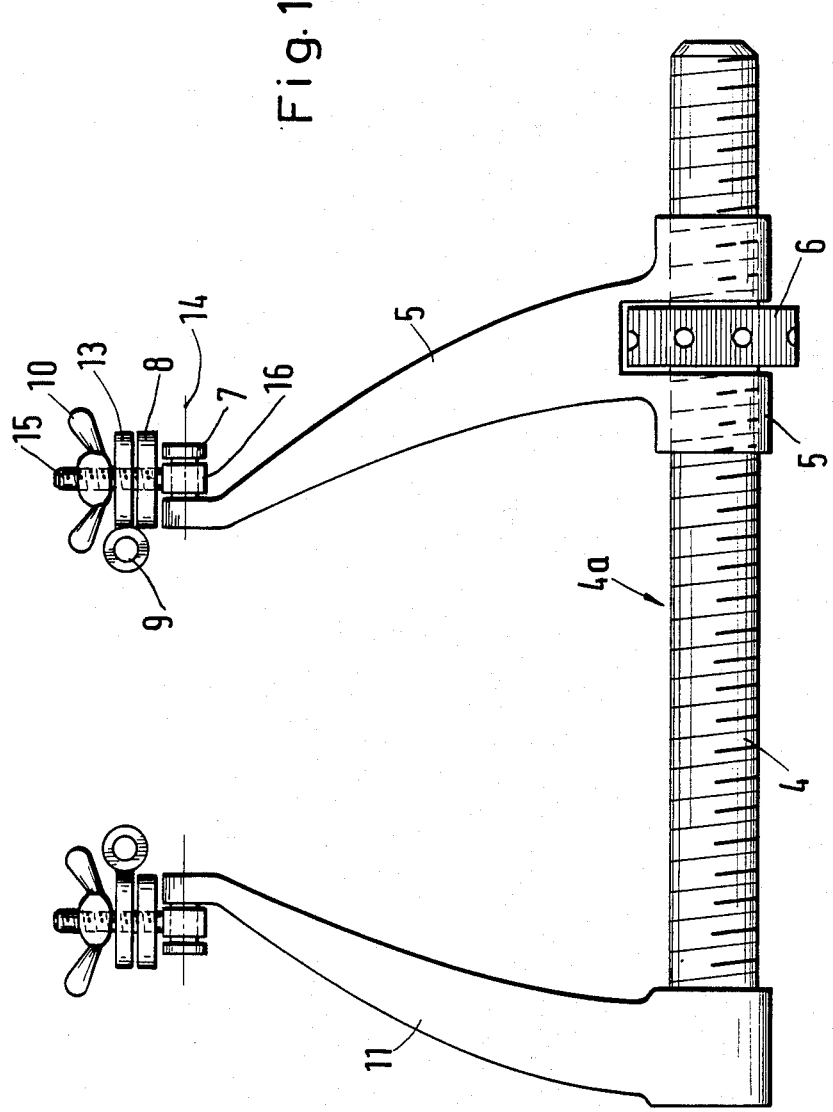
FIG. 1 is a front view of the apparatus of the invention.

As shown in FIG. 1, the apparatus consists of a guide shaft 4 on which the arm 5 is displaceable while the arm 11 is fixed thereon. For displacement of arm 5, the guide shaft is provided with a thread 4a on which a setting nut 6 which is acts on the arm 5. In this way, the distance between the arms 5 and 11 can be changed by turning the setting nut 6. At the end of each arm there is a receiving sleeve 9 which is displaceable in two planes. The construction is such that the receiving sleeve 9 has a resting surface 13 with detents which is detachably fastened on a support surface 8 by means of the screw attachment 10. The support surface 8 has a bushing 16 which is pivotally arranged on a corresponding pin located on the end of the arm. The locking of the sleeve 16 is effected by means of a screw 7 or the like, insofar as this should be necessary. The receiving sleeve 9 can thus be swung around the axis 14. The construction on the arm 11 is the same.

The arms 5 and 11 are somewhat angular in shape and furthermore are also curved in space so that the field of operation is as accessible as possible.

Figure 2:
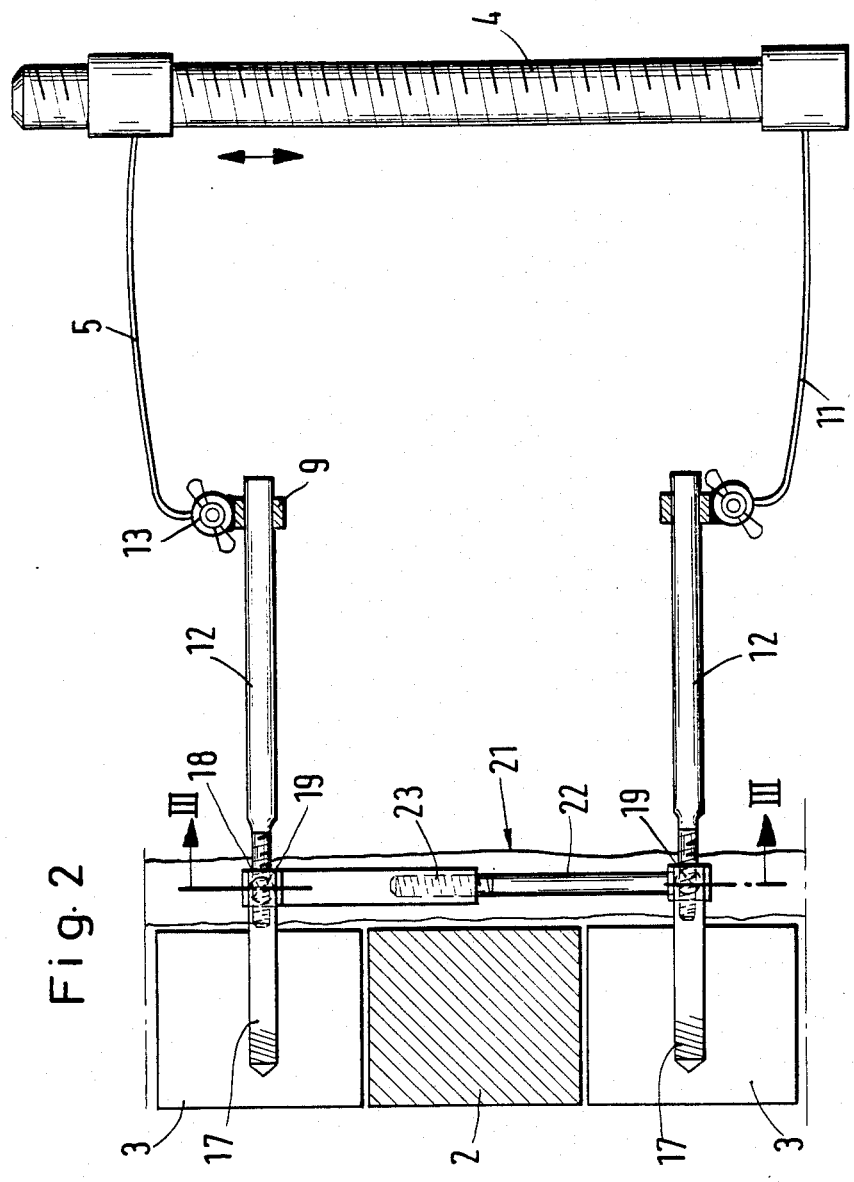
FIG. 2 diagrammatically shows the arrangement of the apparatus on the support bolts, which are arranged in the vertebrae.
Figure 3:
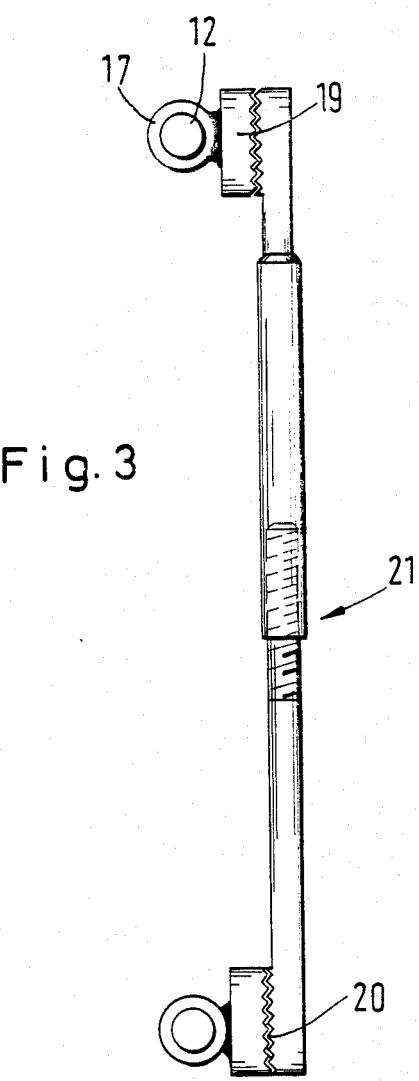
FIG. 3 is a sectional view taken along line III—III in FIG. 2.

FIG. 2 shows the manner of use of the apparatus. The support bolt 17 is screwed in customary manner into the healthy vertebra 3. At its end, each support bolt has a recess 18 with internal thread so that an extension bar 12 can be screwed into the recess. The thread is coaxial to the support bolt. Laterally of the support bolt 17 there is arranged a fastening surface 19 with detents 20 so that the two support bolts can be connected with each other by a turnbuckle 21 for the stabilizing of the vertebra. The turnbuckle 21 consists of a threaded bolt 22 and a threaded sleeve 23 (FIG. 3).

When the spinal column has been straightened by means of the apparatus, it is then stabilized by means of the turnbuckle 21. The extension bars 12 can then be removed. Since relatively short support bolts can thus be used, the subsequent sawing off of these bolts is not necessary and they then can be easily implanted in the musculature.

What is claimed is:

1. Apparatus for straightening a spinal column having damaged vertebrae comprising two spaced support bolts inserted into the vertebrae on opposite sides of the damaged vertebrae, extension rods detachably connected to said support bolts to extend in axial alignment therefrom away from the vertebrae, a sleeve mounted on each said rod remote from the respective said support bolts, an arm for each rod, means connecting each arm to its respective rod via the associated sleeve to provide angular adjustment of the arm relative to the rod about two mutually perpendicular axes, a guide shaft remote from said bolts and said vertebrae, said arms respectively having ends distant from said sleeves, said end of one of the arms being fixed to said guide shaft while said end of the other of the arms is displaceable on said guide shaft axially thereof to permit relative adjustment of said arms and thereby of said rods and said support bolts to effect alignment of the spinal column, and turnbuckle means connected to said support bolts proximate the vertebrae to extend perpendicularly thereof, said turnbuckle means being adjustable in length for applying blocking force on said bolts to stabilize the position thereof produced by the relative adjustment of the arms on said guide shaft.

2. Apparatus as claimed in claim 1 wherein said means which connects each arm to its respective rod via the associated sleeve for angular adjustment of the arm relative to the rod about two mutually perpendicular axes comprises an element with a resting surface secured to said sleeve, said resting surface having detents, a support element having a support surface provided with detents facing the detents of said resting surface and detachably engageable therewith in different relative angular positions of said surfaces, said support element being pivotably mounted on said arm.

3. Apparatus as claimed in claim 1 wherein said guide shaft is threaded, the apparatus further comprising a nut threadably mounted on said shaft and engaging the displaceable arm to displace the latter relative to said shaft.

4. Apparatus as claimed in claim 1 wherein said arms are curved and extend in widening fashion from said rods towards said guide shaft.

5. Apparatus as claimed in claim 1 wherein said arms and said guide shaft are pivotable as a unit relative to said support bolts around said mutually perpendicular axes.

* * * * *